United States Patent [19]
Chang et al.

[11] Patent Number: 5,190,927
[45] Date of Patent: Mar. 2, 1993

[54] HIGH-GLYCERYL, LOW-ACETYL GELLAN GUM FOR NON-BRITTLE GELS

[75] Inventors: Helena C. Chang, Solano Beach; Joseph M. Kobzeff, San Diego, both of Calif.

[73] Assignee: Merck & Co., Inc., Rahway, N.J.

[21] Appl. No.: 727,507

[22] Filed: Jul. 9, 1991

[51] Int. Cl.$^5$ .............................................. C12P 19/04
[52] U.S. Cl. .................................... 514/54; 435/101; 536/123
[58] Field of Search ...................... 536/123; 514/54; 435/101

[56] References Cited

U.S. PATENT DOCUMENTS

| | | | |
|---|---|---|---|
| 4,326,052 | 4/1982 | Kang et al. | 536/1.1 |
| 4,326,053 | 4/1982 | Kang et al. | 536/123 |
| 4,503,084 | 3/1985 | Baird et al. | 426/573 |

OTHER PUBLICATIONS

Kuo et al., *Carbhyd. Res*, vol. 156 (1986), pp. 173–187.
Sanderson et al., "Gellan Gum, a New Gelling Polysacc", pp. 201–210.

*Primary Examiner*—Johnnie R. Brown
*Assistant Examiner*—Pamela S. Webber
*Attorney, Agent, or Firm*—Charles M. Caruso; Richard S. Parr

[57] ABSTRACT

A partially deacylated gellan gum which forms elastic gels having low brittleness, and a process for its preparation.

4 Claims, No Drawings

HIGH-GLYCERYL, LOW-ACETYL GELLAN GUM FOR NON-BRITTLE GELS

BACKGROUND OF THE INVENTION

It is known that heteropolysaccharides can be produced by certain microorganisms. These heteropolysaccharides can function as hydrophilic colloids, and, because of their rheological properties, have been used as thickening and gelling agents for aqueous systems.

Kang et al., U.S. Pat. No. 4,326,053, describes a heteropolysaccharide, gellan gum, prepared by fermentation of *Pseudomones elodea* ATCC 31461, which is useful as a thickening, suspending and stabilizing agent in aqueous systems. The patent also describes a deacylated heteropolysaccharide useful as an agar substitute and for forming rigid, brittle gels. Kang et al., U.S. Pat. No. 4,326,052, describes a clarified deacylated heteropolysaccharide obtained by subjecting the deacylated heteropolysaccharide of U.S. Pat. No. 4,326,053 to filtration, and subsequently adding filtrate to isopropanol, and drying and milling to obtain clarified heteropolysaccharide with low levels of protein.

SUMMARY OF THE INVENTION

The invention includes gellan gum which produces gels having relatively low brittleness or which are non-brittle, and a process for preparing the gum. The process, which includes many of the steps described in U.S. Pat. No. 4,326,053 for producing gellan gum with acyl groups, also includes process steps which enable the gum to retain the ability to produce gels having relatively low or non-brittle character. The process of the invention removes O-acetyl groups from the gellan gum while preserving the presence of O-glyceryl groups. Thus, the gellan gum of the present invention is a partially deacylated gellan gum, having about 3–12%, preferably 4–10%, and more preferably 6–9.5% O-glyceryl groups, and less than 1% O-acetyl groups, preferably zero O-acetyl groups, which is capable of forming elastic gels having low brittleness.

DETAILED DESCRIPTION OF THE INVENTION

The gum of the present invention is a gellan gum having low levels of O-acetyl groups while retaining the desirable quality of being able to produce elastic, non-brittle gels. The gum is prepared according to a modified procedure which includes many of the steps described in U.S. Pat. No. 4,326,053.

The deacylated gellan gum (heteropolysaccharide S-60) described in U.S. Pat. No. 4,326,053 is prepared by fermenting *Pseudomonas elodea* ATCC 31461 in a suitable fermentation medium under suitable conditions to obtain heteropolysaccharide S-60 in the final fermentor. Thereafter, the pH is adjusted to 10 with KOH, and the temperature is maintained at 90°–95° C. for 15 minutes. The pH is then lowered to 6–8 with dilute HCl or $H_2SO_4$, and the gum is recovered using typical filtration and precipitation steps.

While the procedure described in U.S. Pat. No. 4,326,053 is effective for deacylating and clarifying gellan gum, the resulting deacylated gum produces firm, non-elastic, brittle gels (column 7, lines 33–34). According to the process described in U.S. Pat. No. 4,326,053, "a wide range of gel types from very elastic to very brittle is possible, depending on the degree of deacylation" (column 10, lines 4–6).

The present invention is a partially deacylated gellan gum which forms elastic, non-brittle gels.

According to the process of the present invention, deacylated gellan gum suitable for preparing non-brittle, elastic gels is prepared by fermenting *Pseudomonas elodea* ATCC 31461 or suitable mutant in a suitable fermentation medium under suitable conditions to obtain heteropolysaccharide gellan gum in the final fermentor. Thereafter, the pH is adjusted with a base (e.g., NaOH or KOH, preferably KOH) at a rate of 0.08–0.36 g KOH/g gum, preferably 0.12–0.32 g KOH/g gum, more preferably 0.15–0.30 g KOH/g gum or equimolar amounts of other base, and the temperature is maintained at 10°–71° C., preferably 20°–50° C., more preferably 25°–40° C. for a period of time between about 2 minutes and 100 hours, preferably 4–20 hours, more preferably 6–18 hours. The pH is then lowered to 6–8 with dilute HCl or $H_2SO_4$, and the gum is recovered using typical filtration and precipitation steps, depending on whether clarified or non-clarified finished product is desired.

Examples 2–5 illustrate the procedure of the present invention for obtaining gellan gum having essentially zero acetyl groups and retaining high levels of glyceryl groups, from non-deacylated gellan gum (typically 11–13% glycerate and 4–5% acetate).

While the examples are not to be interpreted as limiting the scope of the claim, they illustrate the dramatic reduction in acetyl content which can be achieved following the procedures of the present invention, while retaining a significant quantity of glyceryl content and associated beneficial qualities.

Examples 6 and 7 show procedures for obtaining intermediate levels of both glyceryl and acetyl groups. These procedures differ from the procedures illustrated in Examples 2–5 in three ways: higher process temperature (about 90°–100° C. versus), shorter reaction time (less than ten minutes) and generally lower base (about 0.10 g KOH/g gum or less). The procedure involves heating the broth with less than stoichiometric amount of alkali at a high temperature for a short time in the presence of added salts. Typical conditions include temperatures of $\geq 80°$ C., reaction times of 0.5–4 minutes, and salt concentrations of 1–4 g/l.

Deacylated gellan gum prepared according to the present invention is useful for many of the same purposes as those for which deacylated gellan gum prepared according to U.S. Pat. No. 4,326,053 is useful. However, because the deacylated gellan gum of the present invention retains the ability to form elastic, non-brittle gels, the ability not retained by the deacylated gellan gum prepared according to U.S. Pat. No. 4,326,053, the present invention gellan gum can be used in systems requiring elastic, non-brittle gels without using additional components such as xanthan gum and galactomannan or glucomannan gum, which are required when the deacylated gellan gum of U.S. Pat. No. 4,326,053 is used. The increased diversity makes the gums of the present invention especially useful in food systems.

The gums of the subject application may be used in many food gelling and thickening applications including but not limited to confections, jams and jellies, fabricated foods, water-based gels, pie fillings and puddings, pet foods, icings and frostings, and dairy products.

Fermentation Conditions

Gellan gum is produced during the aerobic fermentation of suitable aqueous nutrient media under controlled conditions via the inoculation with the organism *Pseudomonas elodea* ATCC 31461. The media contain sources of carbon, nitrogen and inorganic salts. The gum may also be prepared with a *Pseudomonas elodea* ATCC 53967, a mutant of ATCC 31461, or other suitable strains.

In general, carbohydrates (for example glucose, fructose, maltose, sucrose, xylose, mannitol and the like) can be used either alone or in combination as sources of assimilable carbon in the nutrient medium. The exact quantity of the carbohydrate source or sources utilized in the medium depend in part upon the other ingredients of the medium. In general, the amount of carbohydrate usually varies between about 2% and 4% by weight of the medium. In general, many proteinaceous materials may be used as organic nitrogen sources in the fermentation process.

Suitable nitrogen sources include, for example, yeast hydrolysates, soybean meal, cottonseed flour, hydrolysates of casein, corn steep liquor, distiller's solubles and the like. The sources of nitrogen, either alone or in combination, are used in amounts ranging from about 0.05% to 0.2% by weight of the aqueous medium.

Among the nutrient inorganic salts which can be incorporated in the culture media are the customary salts capable of yielding sodium, potassium, ammonium, calcium, phosphate, sulfate, chloride, carbonate, and like ions. Also included are trace metals such as cobalt, manganese, iron and magnesium.

It should be noted that the media described in the examples are merely illustrative of the wide variety of media which may be employed, and are not intended to be limitative.

The fermentation is carried out at temperatures ranging from about 25° C. to 35° C. For optimum results, it is preferable to conduct the fermentation at temperatures of from about 28° C. to 32° C. The pH of the nutrient media for growing the Pseudomonas culture and producing the polysaccharide can vary from about 6 to 8.

Although the polysaccharide is produced by both surface and submerged culture, it is preferred to carry out the fermentation in the submerged state.

A small scale fermentation is conveniently carried out by inoculating a suitable nutrient medium with the culture and, after transfer to a production medium, permitting the fermentation to proceed at a constant temperature of about 30° C. on a shaker for several days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 30° C. for 1-2 days, or until growth is satisfactory, and some of the resulting growth is used to inoculate either a second stage seed or the production medium. Intermediate stage seed flasks, when used, are developed in essentially the same manner, that is, part of the contents of the flask from the last seed stage are used to inoculate the production medium. The inoculated flasks are shaken at a constant temperature for several days, and at the end of the incubation period the contents of the flasks are recovered by precipitation with a suitable alcohol such as isopropanol.

For large scale work, it is preferable to conduct the fermentation in suitable tanks provided with an agitator and a means of aerating the fermentation medium. According to this method, the nutrient medium is made up in the tank and sterilized by heating at temperatures of up to about 121° C. Upon cooling, the sterilized medium is inoculated with a previously grown seed of the producing culture, and the fermentation is permitted to proceed for a period of time as, for example, from 2 to 4 days while agitating and/or aerating the nutrient medium and maintaining the temperature at about 30° C. This method is particularly suited for preparation of large quantities.

The heteropolysaccharide is produced at a conversion efficiency of about 50%, resulting in a very high viscosity beer (4,000 to 8,000 cP).

Post-fermentation Treatment

The fermentation broth containing acylated heteropolysaccharide is maintained at a temperature of between about 10° C. and 71° C., preferably 20°-50° C., more preferably 25°-40° C., for a period of time of about 2 minutes to 100 hours, preferably 4-20 hours, more preferably 6-18 hours. pH is controlled using, for example, 0.08-0.36 g KOH/g gum, preferably 0.12-0.32 g KOH/g gum, more preferably 0.15-0.30 g KOH/g gum or equimolar amounts of sodium carbonate or sodium hydroxide to obtain the basic condition. Deacylation readily occurs, while loss of O-glyceryl groups occurs at a relatively slower rate.

EXAMPLE 1

Fermentation Procedure for Producing Heteropolysaccharide

*Pseudomonas elodea*, ATCC 31461, grows quite well on NA or YM agar, which are used routinely for culture maintenance. The incubation temperature is 30° C.

Flask seeds are prepared in YM broth incubated at 30° C. When inoculated with a fresh plate culture, the YM broth cultures give good growth and gum formation by 24 hours.

The fermentation seed medium is the same as final fermentor medium, using one-gallon fermentors as seed vessels.

3.0% Glucose
0.01% $MgSO_4.7H_2O$
0.09% $NH_4NO_3$
0.05% Promosoy 1 ml/L HoLe salts
1 ppm Fe++
0.05% $K_2HPO_4$ pH control=KOH HoLe salts are a trace element solution containing tartrate, magnesium molybdate, $CoCl_3$, $ZnCl_2$, $CuCl_2$, boric acid, manganese chloride and ferrous sulfate.

The heteropolysaccharide produced by *P. elodea*, prior to deacylation, is composed of about 50% carbohydrate gellan polysaccharide and 50% insoluble material which comprises cellular debris. The polysaccharide has the following tetrasaccharide repeating unit:

→3)—βD—Glcp—(1→4)—β—D—Glcp—(1→
4)—β—D—Glcp—(1→4)—a—L—Rhap—(1→

In addition, the polysaccharide contains O-acetyl and O-glyceryl groups as the O-glycosidically linked esters.

The acetyl and glyceryl contents of the polysaccharide are determined by hydrolysis with trifluoroacetic acid overnight at 100° C., followed by high pressure liquid chromatography.

A most significant property of the heteropolysaccharide, both in its native state and after deacylation, is the formation of thermo-reversible gels after heating and cooling.

Gels prepared with the native or acylated polysaccharides are characterized as weak and elastic whereas gels with completely deacylated polysaccharide are characterized as strong brittle gels. Varying degrees of deacylation provide comparably varying degrees of gel brittleness.

Gels are prepared using gums of the present invention and tested in accordance with standard texture profile analysis. Gum is added to the vortex of stirring distilled water and mixed. After thorough mixing, the mixture is heated, e.g. to 85° C., and mixed for an additional amount of time. Calcium chloride stock solution is then added, followed by addition of more distilled water. The mixture is then poured and allowed to stand at room temperature for 20–24 hours.

Texture profile analysis (Sanderson et al., 1988 *Gums and Stability for the Food Industry*, vol. 4, pp. 219–227) is a compression test of free standing gels. Samples are compressed twice to 20% of their original height at a rate of 2 inches/minute. Modulus, hardness, brittleness and elasticity are measured and shown in Examples 2–7.

Modulus (M) (Newtons/cm$^2$) is the initial slope of the stress-strain curve. Hardness (H) (pounds) is the maximum force during the first compression cycle. Brittleness (B) (% of original height) is the strain at the first significant drop in stress during the first compression cycle. Elasticity (E) (% of original height) is the height of the gel sample after the first compression cycle.

Texture profile analysis on non-deacylated gellan gum (no KOH treatment, 12.9% (wt.) glycerate and 4.7% (wt.) acetate groups) and on fully deacylated gellan gum (no glycerate and no acetate groups) shows the following:

| Gellan Type | M | H | B | E |
|---|---|---|---|---|
| Non-deacylated | 0.2 | 5.0 | 79.8 | 68.3 |
| Fully deacylated | 14.4 | 7.1 | 28.2 | 13.1 |

Examples 2–5 illustrate procedures for making high glycerate/low acetate gellan gum.

EXAMPLE 2

Heteropolysaccharide Deacylation

The fermentation broth obtained in Example 1, containing acylated heteropolysaccharide, is subjected to the following treatment:
  a. A broth containing approximately 1.4% gellan polysaccharide is maintained at 25° C.
  b. The pH is raised by the addition of KOH according to the schedule given below.
  c. The temperature is maintained for a period of 18 hours.
  d. The pH is adjusted to 6–8 with HCl or H$_2$SO$_4$.
  e. The broth is heated to 95° C., and is precipitated with isopropanol, and the fibers are dried at 50° C. for about one hour.

| KOH level g/g gum | M | H | B | E | Glycerate % wt | Acetate % wt |
|---|---|---|---|---|---|---|
| 0.03 | 0.4 | 4.3 | 79.6 | 56.2 | 11.3 | 4.7 |
| 0.06 | 0.4 | 3.1 | 79.4 | 45.9 | 11.6 | 3.9 |
| 0.12 | 1.2 | 12.0 | 73.4 | 40.7 | 9.1 | 0.3 |
| 0.19 | 13.3 | 9.8 | 30.9 | 8.4 | 0.3 | 0.2 |
| 0.24 | 11.9 | 6.9 | 47.0 | 15.9 | 0.3 | 0.2 |

EXAMPLE 3

Heteropolysaccharide Deacylation

Heteropolysaccharide in the fermentation broth obtained according to the procedure described in Example 1 was deacylated according to the following treatment.
  a. A solution of broth containing approximately 1.4% g of the gellan polysaccharide is maintained at 36° C.
  b. The pH is raised by the addition of KOH according to the schedule given below.
  c. The temperature is maintained for a period of 18 hours.
  d. The pH is adjusted to 6–8 with HCl or H$_2$SO$_4$.
  e. The broth is heated to 95° C.
  f. Ten grams per liter of filter aid are added to the material to be filtered.
  g. The material was filtered through a pre-heated 730 cm$^2$ pressure filter with about 6 mm of filter aid and about 20–30 psi.
  h. The filtrate is precipitated with isopropanol immediately to prevent gelation, and the fibers are dried at 50° C. for about one hour.

| KOH level g/g gum | M | H | B | E | Glycerate % wt | Acetate % wt |
|---|---|---|---|---|---|---|
| 0.15 | 0.3 | 1.0 | 70.5 | 29.4 | 8.9 | 0.2 |
| 0.22 | 0.5 | 2.9 | 51.2 | 32.5 | 6.5 | 0.2 |
| 0.30 | 1.5 | 2.7 | 40.6 | 15.2 | 4.6 | 0.2 |
| 0.37 | 3.6 | 2.1 | 31.7 | 13.0 | 3.1 | 0.2 |

EXAMPLE 4

Heteropolysaccharide Deacylation

Heteropolysaccharide in the fermentation broth obtained according to the procedure described in Example 1 was deacylated according to the general procedure described in Example 2 except that in step (a), the temperature is 25°, 40°, and 100° C. for different samples, in step (b), the KOH used is 0.12 g/g gum, and in step (c), the time is 18 hours, 6 hours, and 4 minutes for different samples.

| Temp °C. | Time | M | H | B | E | Glycerate % wt. | Acetate % wt |
|---|---|---|---|---|---|---|---|
| 25 | 18 hrs | 1.1 | 12.0 | 73.4 | 40.7 | 9.1 | 0.3 |
| 40 | 6 hrs | 1.1 | 12.6 | 74.2 | 32.3 | 9.4 | 0.5 |
| 100 | 4 min | 2.5 | 6.8 | 47.9 | 12.4 | 2.9 | 2.0 |

EXAMPLE 5

Heteropolysaccharide Deacylation

Heteropolysaccharide in the fermentation broth obtained according to the procedure described in Example 1 was deacylated according to the general procedure described in Example 3 except that in step (b), the KOH level is 0.30 g/g gum, and in step (c), the time is 2, 3, and 6 hours for different samples.

| Time, hr | M | H | B | E | Glycerate % wt | Acetate % wt |
| --- | --- | --- | --- | --- | --- | --- |
| 2 | 0.2 | 7.3 | 77.8 | 53.8 | — | — |
| 3 | 0.5 | 30.6 | 79.0 | 48.5 | 8.3 | 0 |
| 6 | 0.6 | 16.4 | 75.5 | 25.2 | 6.3 | 0 |

Examples 6 and 7 illustrate procedures for making gellan gum with intermediate levels of both glycerate and acetate.

EXAMPLE 6

Heteropolysaccharide Deacylation

The fermentation broth obtained in Example 1, containing acylated heteropolysaccharide, is subjected to the following treatment:

a. A broth containing approximately 1.4% gellan polysaccharide is maintained at 90°–100° C.
b. The pH is raised by the addition of KOH according to the schedule given below.
c. The temperature is maintained for a period of 4 minutes.
d. The pH is adjusted to 6–8 with HCl or $H_2SO_4$.
e. The broth is precipitated with isopropanol, and the fibers are dried at 50° C. for about one hour.

| KOH level g/g gum | M | H | B | E | Glycerate % wt | Acetate % wt |
| --- | --- | --- | --- | --- | --- | --- |
| 0.03 | 0.6 | 7.5 | 79.4 | 52.7 | 10.6 | 4.8 |
| 0.06 | 0.7 | 8.6 | 75.3 | 32.1 | 8.3 | 4.2 |
| 0.11 | 1.7 | 10.2 | 59.1 | 13.8 | 4.1 | 2.1 |
| 0.12 | 2.5 | 6.8 | 47.9 | 12.4 | 2.9 | 2.0 |
| 0.24 | 14.0 | 8.0 | 28.5 | 10.2 | 0.3 | 0.2 |
| 0.36 | 14.7 | 7.4 | 24.5 | 9.4 | 0.3 | 0.3 |

EXAMPLE 7

Heteropolysaccharide Deacylation

Heteropolysaccharide in the fermentation broth obtained according to the procedure described in Example 1 was deacylated according to the following treatment:

a. A broth containing approximately 1.4% gellan polysaccharide is maintained at 95° C.
b. The pH is raised by the addition of 0.05 KOH/g gum.
c. Salt is added according to the schedule given below.
d. The temperature is maintained for a period of 0.5 minutes.
e. The pH is adjusted to 6–8 with HCl or $H_2SO_4$.
f. Ten grams per liter of filter aid are added to the material to be filtered.
g. The material was filtered through a pre-heated 730 $cm^2$ pressure filter with about 6 mm of filter aid and about 20–30 psi.
h. The filtrate is precipitated with isopropanol immediately to prevent gelation, and the fibers are dried at 50° C. for about one hour.

| Salt | M | H | B | E | Glycerate % wt | Acetate % wt |
| --- | --- | --- | --- | --- | --- | --- |
| none | 0.2 | 3.3 | 71.6 | 33.5 | 6.4 | 3.7 |
| 4 g/l NaCl | 0.2 | 5.3 | 78.4 | 44.9 | 6.3 | 2.6 |
| 4 g/l KCl | 0.2 | 3.9 | 73.2 | 32.7 | 8.5 | 3.8 |
| 1 g/l $CaCl_2.2H_2O$ | 0.2 | 5.5 | 78.8 | 57.2 | 10.0 | 3.9 |

Examples 8–10 illustrate uses of the gum of the present invention.

EXAMPLE 8

Agar Replacement (Nutrient Agar)

| Ingredients | Weight, grams |
| --- | --- |
| Beef Extract | 3 |
| Peptone | 5 |
| Clarified gellan, fully deacylated | 4.9 |
| Clarified gellan, high glycerate/low acetate | 2.1 |
| $MgCl_2.6H_2O$ | 0.75 |

Procedure

1. Suspend the ingredients in 1 liter distilled or deionized water.
2. Autoclave for 15 minutes at 15 pounds pressure (121° C.).
3. Dispense as desired.

EXAMPLE 9

Low Sugar Fruit Spreads

| Ingredients | Percent |
| --- | --- |
| Apricots, canned, drained | 53.773 |
| Sugar, granular | 29.877 |
| Citric acid, anhydrous | 0.996 |
| Sodium citrate, hydrous granular | 0.398 |
| Gellan gum, fully deacylated | 0.100 |
| Gellan gum, High glycerate/low acetate | 0.100 |
| Potassium sorbate, powder | 0.050 |
| FD&C Yellow #5 | 0.010 |
| FD&C Yellow #6 | 0.002 |

Procedure

1. Combine apricots and water.
2. Combine dry ingredients except citric acid, and stir into apricot mixture. Stir and heat apricot mixture to boiling and hold for 1 minute. Stir in citric acid.
3. Continue heating and stirring until mixture reaches 38% soluble solids.
4. Pour into sterilized jars and seal.
5. Hold for 5 minutes in a boiling water bath.
6. Cool at room temperature or under refrigeration.

EXAMPLE 10

Dessert Gels

| Ingredients | Percent |
| --- | --- |
| Water | 85.83 |
| Sugar, granular | 13.07 |
| Adipic acid, powdered | 0.58 |
| Sodium citrate, hydrous, fine granular | 0.27 |

| Ingredients | Percent |
| --- | --- |
| Gellan gum | 0.20 |
| Artificial strawberry flavor | 0.04 |
| FD&C Red #40 | 0.01 |

Procedure

1. Bring water to a boil.
2. Add the preblended dry ingredients to the boiling water.
3. Continue heating and mix for 1-2 minutes.
4. Pour into serving dishes or molds.
5. Cool at room temperature or under refrigeration.

Test Results

TPA values for dessert gels made with both fully deacylated gellan and high glycerate/low acetate gellan are shown below:

| Gellan Type | M | H | B | E |
| --- | --- | --- | --- | --- |
| fully Deacyl. | 1.7 | 2.2 | 36.3 | 18.2 |
| high glycerate/low acetate | 0.4 | 2.1 | 75.7 | 26.3 |

What is claimed is:

1. Partially deacylated gellan gum which comprises between 0% and less than about 1% acetyl groups, and about 3-12% glyceryl groups, derived from *Pseudomonas elodea* ATCC 31461 grown in a suitable fermentation medium.

2. Partially deacylated gellan gum of claim 1 which comprises between 0% and less than about 1% acetyl groups, and about 4-10% glyceryl groups.

3. Partially deacetylated gellan gum of claim 2 which comprises between 0% and less than about 1% acetyl groups and about 6-9.5% glyceryl groups.

4. A gel composition comprising the gum of claim 1 and a carrier.

* * * * *